(12) United States Patent
Ward et al.

(10) Patent No.: US 7,146,202 B2
(45) Date of Patent: Dec. 5, 2006

(54) COMPOUND MATERIAL ANALYTE SENSOR

(75) Inventors: W. Kenneth Ward, Portland, OR (US); Richard G. Sass, Portland, OR (US)

(73) Assignee: iSense Corporation, Portland, OR (US)

( * ) Notice: Subject to any disclaimer, the term of this patent is extended or adjusted under 35 U.S.C. 154(b) by 0 days.

(21) Appl. No.: 10/869,133

(22) Filed: Jun. 16, 2004

(65) Prior Publication Data

US 2005/0004438 A1    Jan. 6, 2005

Related U.S. Application Data

(60) Provisional application No. 60/479,141, filed on Jun. 16, 2003.

(51) Int. Cl.
*A61B 5/00* (2006.01)
*A61B 5/05* (2006.01)

(52) U.S. Cl. ............... 600/345; 600/347; 600/365

(58) Field of Classification Search ......... 600/345–350
See application file for complete search history.

(56) References Cited

U.S. PATENT DOCUMENTS

| | | | |
|---|---|---|---|
| 3,957,613 A * | 5/1976 | Macur ................ 204/412 |
| 4,805,624 A * | 2/1989 | Yao et al. ............. 600/345 |
| 5,165,407 A | 11/1992 | Wilson et al. ........... 128/635 |
| 5,310,469 A | 5/1994 | Cunningham et al. . 204/403.09 |
| 5,645,710 A * | 7/1997 | Shieh ................... 205/778 |
| 5,842,983 A | 12/1998 | Abel et al. ............. 204/403.1 |
| 5,989,409 A * | 11/1999 | Kurnik et al. ............ 205/792 |
| 6,104,940 A * | 8/2000 | Watanabe et al. ........... 600/345 |
| 6,484,045 B1 | 11/2002 | Holker et al. ............. 600/345 |
| 6,501,976 B1 * | 12/2002 | Sohrab .................. 600/347 |
| 6,915,147 B1 * | 7/2005 | Lebel et al. ............. 600/322 |
| 2002/0137998 A1 * | 9/2002 | Smart et al. ............. 600/347 |
| 2002/0188184 A1 * | 12/2002 | Kiser et al. ............. 600/345 |
| 2005/0096519 A1 * | 5/2005 | DeNuzzio et al. ......... 600/345 |
| 2005/0203364 A1 * | 9/2005 | Monfre et al. ........... 600/365 |

\* cited by examiner

*Primary Examiner*—Robert L. Nasser
(74) *Attorney, Agent, or Firm*—Schwabe Williamson & Wyatt

(57) ABSTRACT

A sensing element adapted to, at least in part, be inserted into a mammalian body. The sensing element is made up of a core of a structurally robust metal and a plated portion made of an electrochemically active metal conjoined to at least a portion of the core. This sensing element may be used as part of a method for the continuous or intermittent monitoring of an analyte within a mammalian body. The method includes inserting at least a portion of the sensing element into the mammalian body and measuring any electric current produced by at least of portion of the sensor.

12 Claims, 1 Drawing Sheet

COMPOUND MATERIAL ANALYTE SENSOR

RELATED APPLICATIONS

The present patent application claims priority from provisional application Ser. No. 60/479,141, filed Jun. 16, 2003, which is incorporated by reference as if fully set forth herein.

BACKGROUND OF THE INVENTION

With the advent of indwelling wire sensors has come the danger to the patient of having a cylindrical wire sensor fatigue from the flexure caused by bodily movement and break off inside the body. Under such circumstances a wire sensor can move through tissue relatively quickly and in an unpredictable manner, potentially posing a threat to the delicate internal organs.

Unfortunately, the typical metal used for such a wire sensor is platinum, which is electrochemically active and generally very useful in sensing applications. Platinum, however, is a weak metal that is easily broken with only a little flexure. Moreover, the electrochemical nature of platinum surfaces is only imperfectly understood. Efforts to make sensors from very thin platinum wires that are stranded together, thereby providing greater flex resistance, have encountered negative effects on the biochemical reactivity of the more complex platinum surface.

Also, platinum is very expensive costing on the order of $25–$30 per gram. For a multiple use sensing assembly incorporating a multiplicity of single use sensing elements, this may be a considerable expense. Also, for sensing elements that double as skin piercing lancets, greater strength is needed than may be available from a small diameter platinum wire. Even for sensors that are to be worn for a few days, the cost of the platinum portion of the sensor can place a strain on the overall budget for a production run of sensors.

SUMMARY

In a first separate aspect, the present invention is a sensor adapted to, at least in part, be inserted into a mammalian body. The sensor comprises a core of a structurally robust material and a plated portion, comprising an electrochemically active metal plated onto at least a portion of the core.

In a second separate aspect, the present invention is a method for the continuous monitoring of an analyte within a mammalian body. The method includes inserting at least a portion of a sensor into the mammalian body, continuously monitoring any electric current produced by at least a portion of the sensor. The sensor, in turn, includes a core of structurally robust material and a plated portion, comprising an electrochemically active metal plated onto at least a portion of the core.

In a third separate aspect, the present invention is a method of producing a sensor that is adapted to, at least in part, be inserted into a mammalian body and dwell within the mammalian body for at least an hour. The method comprises applying a layer of an electrochemically active metal onto at least a portion of a core made of a structurally robust material.

The foregoing and other objectives, features and advantages of the invention will be more readily understood upon consideration of the following detailed description of the invention, taken in conjunction with the accompanying drawings.

DETAILED DESCRIPTION OF THE PREFERRED EMBODIMENT

Figure 1:
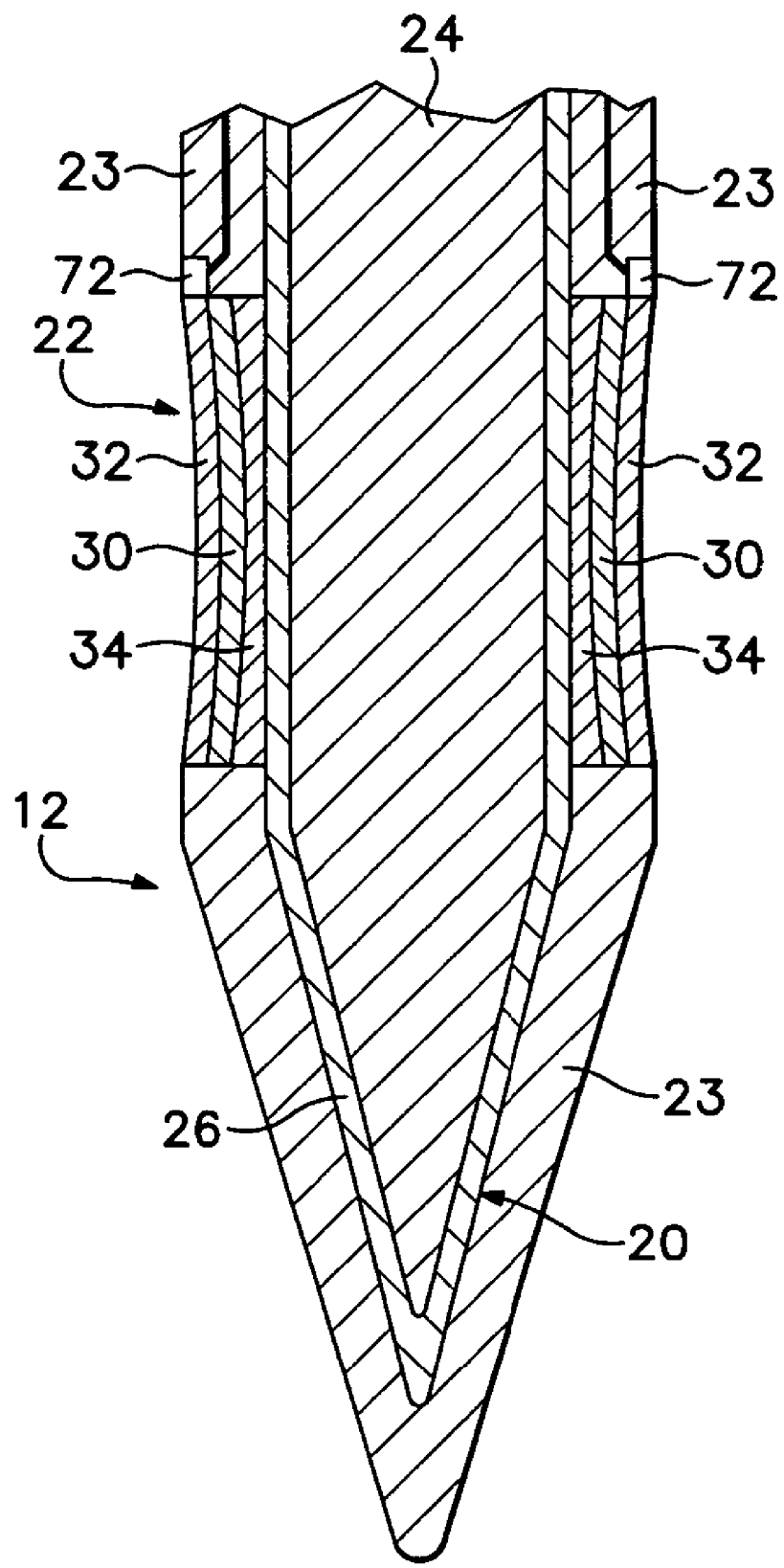
FIG. 1 is a side cross-sectional view of a sensing element according to the present invention.

Referring to FIG. 1, sensing element 12 includes a bimetallic wire 20 that, when a voltage is placed on wire 20 relative to a reference electrode, in conjunction with a membrane system 22 reacts to the presence of glucose and oxygen (in some preferred embodiments, glucose only) by creating a current. Wire 20 is coated with a protective layer 23, made of durable, non-toxic material such as polyimide, except for where coated by membrane system 22. In production, protective layer 23 is dip-coated onto wire 20 and then removed, preferably with an excimer or ND:YAG laser in the area in which membrane system 22 is to be applied. In other preferred embodiments there is no protective layer 23 and the entire wire 20 is coated with membrane assembly 22.

Wire 20 may have a diameter on the order of 227 microns and has a wire core 24 of structurally robust material such as stainless steel or tantalum that is 226 microns thick and an electrochemically active layer 26, such as platinum, that is less than a micron thick. In an alternative preferred embodiment, wire 20 is 177 microns in diameter, core 24 is 157 microns in diameter and is made of tantalum and layer 26 is 10 microns thick and is a platinum foil that has been joined to core 24.

To expand somewhat on the specific construction, wire core 24 may be of any structurally robust material, such as tantalum, stainless steel or nitinol, which is an alloy of nickel and titanium. Tantalum and nitinol, although both fairly expensive, are desirable because they are both naturally flexible. This is of particular importance if sensing element 12 is to be inserted in a patient and worn for a period of days. In addition, core 24 could be made of polymeric material or a glass fiber. Electrochemically active layer 26 may be made of one of the noble metals, such as platinum, palladium, gold or a combination of any of the aforesaid with iridium. In a set of preferred embodiments, other noble metals are used in layer 26.

A number of strategies are possible for making plated core or wire 20. In one method, a tube of platinum is prepared and molten stainless steel, tantalum or nitinol is poured inside of it, to form a filled tube. The filled tube is then drawn through progressively smaller apertures, until its diameter reaches the desired thickness. This produces a filled tube that typically is far longer than is necessary, but is available to be cut to whatever length is desired. Another issue with drawn filled tubes is that it is difficult to reduce the thickness of the layer of platinum to less than 20 microns. This increases the expense because it forces the use of a greater than otherwise necessary amount of platinum.

Another method starts with a robust metal wire that is then electroplated with platinum or another noble metal, such as palladium. In this method the robust metal wire is typically negatively charged to form a cathode. A plating solution bath is positively charged to form an anode. Typically the first step is to plate the stainless steel with an intermediate layer that bonds well to both stainless steel and platinum. Typically this layer is gold, although it has been found to be advantageous to plate a first intermediate layer of nickel, plate gold over this layer of nickel and finally plate the gold with platinum. The plating solution may be either acid or alkaline.

In one preferred method, a core of nitinol was used. In this method gold is plated over the nitinol. As nitinol oxidizes very rapidly, hydrofluoric acid is included in the gold bath to strip away any oxidation that may have formed on the nitinol.

In yet another preferred method, a core of robust metal is circumferentially clad in noble metal foil. Although with this method a 1 micron cladding cannot be achieved, cladding in the neighborhood of 5 to 15 microns is possible. One advantage of a thicker cladding is that it is harder for pinholes to extend all the way through.

Another possibility is coating by way of plasma vapor deposition, in which a metallic vapor is created and coats the core 24. First a wire of structurally robust material 24, such as tantalum, is passivated, meaning that a thin layer of oxide is created on the exterior of the wire. Then platinum is vaporized in a plasma environment, and deposition of layer 26 on the tantalum wire results. Using this technique a robust coating 26 of platinum (or another electrochemically active metal) can be created on an underlying tantalum (or other structurally robust metal) core. Moreover, the layer 26 of platinum is electrically isolated from the structurally sound material 24 by a layer of oxide, which is nonconducting. Accordingly, if there is a pinhole in the platinum 26, there will nevertheless be no electrical contact between the body fluid and the underlying core 24 of structurally sound material. If body fluid were to contact core 24, unpredictable electrical activity could result, potentially corrupting the measurement. In a similar manner, an electrochemically active metal may be deposited on a continuous wire of structurally sound metal, designed to host many sensing sites.

Also, sputtering, in which free metallic charged particles are created, may be used to perform the coating or cladding step. Both plasma vapor deposition and sputtering are well known in the art.

In yet another preferred method of producing a thin platinum coating over stainless steel, a strike, or extremely thin (<5 microns) coating of gold is first electroplated onto the stainless steel core. Then, platinum is electroplated in a bath having a current density on the order of 40 amperes/ft$^2$ or less. It is important to electroplate with a comparatively low current density, causing a slow buildup of platinum, in order to prevent uneven growth of the platinum layer.

The membrane system 22 must perform a number of functions. First, it must provide an enzyme that reacts with glucose and oxygen (or glucose only in some preferred embodiments) to form an electrolyte. A reactive layer 30 of glucose oxidase, glutaraldehyde and albumin, which produces hydrogen peroxide when contacted by glucose and oxygen, performs this function. Other enzymes may be used for this process and fall within the scope of this invention.

Second, because glucose is far more prevalent in the blood and other body fluids than oxygen, system 22 must include a membrane placed over the reactive layer 30 to permit a greater permeation of oxygen than glucose, so that the glucose concentration measurement is not limited by the oxygen concentration in the immediately surrounding tissue. This function is performed by a permselective hard block/soft block copolymer layer 32. This layer is of the type described in U.S. Pat. Nos. 5,428,123; 5,589,563 and 5,756,632, which are hereby incorporated by reference as if fully set forth herein. Layer 32 is preferably less than 10 microns thick, to permit rapid permeation by glucose and oxygen.

Third, membrane system 22 must prevent interferents, such as acetaminophen, from corrupting the measurement by causing current flow unrelated to the presence of glucose. This function is performed by an inner interferent reducing layer 34 of a compound such as sulfonated polyether sulfone, 3-amino-phenol, or polypyrrole, which quickly permits the permeation of the hydrogen peroxide, which causes the current flow indicative of the concentration of glucose. Persons skilled in the relevant arts will readily recognize that quick permeation is highly desirable in a briefly indwelling sensor so that a measurement may be quickly obtained.

To produce sensing element 12, first the interferent reducing layer 34 of 3-amino-phenol is solution-coated or electro polymerized onto the surface of platinum plating 26. Layer 34 may be from a few nanometers to 2 microns thick, to permit rapid permeation by $H_2O_2$ ions, thereby reacting very quickly to glucose concentration. Over this the reactive layer 30 of glucose oxidase is dip-coated or electrodeposited. Glutaraldehyde is deposited on the glucose oxidase to immobilize the glucose oxidase. The sensor is dip coated in the soft block/hard block copolymer 32. In the finished product, the surface of the sensing region 22 is slightly depressed relative the remainder of the surface of sensing element 12. In one embodiment, the glucose oxidase 30 is applied before layer 34, which is electrodeposited through layer 30. A voltage is placed between contacts 72 at the beginning of the measurement process. When electrical current flows between contacts 72, this indicates that body fluid has completely wet membrane system 22 and serves as a signal to place a voltage on conductor 24.

In one preferred embodiment, a layer of absorbent metal is included over membrane system 22. In use, sensing element 12 may be either inserted into the body for a number of days and may provide a multiplicity of glucose measurements or may be used as a single use sensing element. When used for a single use, sensing element 12 may be part of a multiple sensing element assembly. The measurement of glucose concentration may occur when sensing element 12 is briefly indwelling, for example, indwelling for less than 3 minutes, or may occur after it has been withdrawn, with body fluid retained on sensing element 12 being tested. A single use element 12 is typically optimized to provide a fast readout, whereas a sensing element that dwells within the body for days is typically optimized for accuracy over time and to satisfy the greater safety challenge posed by an indwelling device.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A method for measuring the concentration of an analyte within an animal body having body fluids, comprising:
   (a) providing a sensor having:
      (i) a structurally flexible core having an outer surface; and
      (ii) a layer of electrochemically active metal surrounding, covering, and in contact with said outer surface of said core;
   (b) placing at least a portion of said sensor into said animal body; and
   (c) measuring any electric current produced by said sensor and forming a measurement of analyte concentration based on said current measurement.

2. The method of claim 1, wherein said electrochemically active metal comprises a noble metal.

3. The method of claim 2, wherein said noble metal comprises at least one of platinum, palladium, and gold.

4. The method of claim 1, wherein said core comprises nitinol.

5. The method of claim 1, wherein said core comprises tantalum.

6. The method of claim 1, wherein said layer of electrochemically active metal is adapted to provide at least one sensing surface.

7. The method of claim 1, wherein said forming a measurement of analyte concentration comprises forming a measurement using body fluid retained on said sensor after said sensor is withdrawn from said animal body.

8. The method of claim 1, wherein said placing at least a portion of said sensor into said animal body comprises placing said at least a portion of said sensor in said animal body for less than 3 minutes.

9. The method of claim 1, wherein said placing at least a portion of said sensor into said animal body comprises placing said at least a portion of said sensor in said animal body for at least 24 hours.

10. The method of claim 1, wherein said analyte comprises glucose.

11. The method of claim 1, wherein said core further comprises at least a first end, and wherein said electrochemically active layer further surrounds, covers, and is in contact with said at least a first end of said core.

12. A method for measuring the concentration of an analyte within an animal body having body fluids, comprising:
  (a) providing a sensor having:
    (i) a core of polymeric material or glass fiber having an outer surface; and
    (ii) a layer of electrochemically active metal surrounding, covering, and in contact with said outer surface of said core;
  (b) placing at least a portion of said sensor into said animal body; and
  (c) measuring any electric current produced by said sensor and forming a measurement of analyte concentration based on said current measurement.

* * * * *